US011737791B2

(12) United States Patent
Biedermann et al.

(10) Patent No.: US 11,737,791 B2
(45) Date of Patent: Aug. 29, 2023

(54) SYSTEM AND INSTRUMENT FOR CORRECTING A POSITION OF BONES, BONE PARTS, OR VERTEBRAE

(71) Applicant: BIEDERMANN TECHNOLOGIES GMBH & CO. KG, Donaueschingen (DE)

(72) Inventors: Timo Biedermann, Trossingen (DE); Achim Schünemann, VS-Mühlhausen (DE); Marc Mundhenke, Gottmadingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 16/594,691

(22) Filed: Oct. 7, 2019

(65) Prior Publication Data

US 2020/0107862 A1    Apr. 9, 2020

Related U.S. Application Data

(60) Provisional application No. 62/743,347, filed on Oct. 9, 2018.

(30) Foreign Application Priority Data

Oct. 9, 2018  (EP) .................................... 18199467

(51) Int. Cl.
*A61B 17/70*   (2006.01)
*A61B 17/68*   (2006.01)

(52) U.S. Cl.
CPC ...... *A61B 17/7037* (2013.01); *A61B 17/7034* (2013.01); *A61B 17/7091* (2013.01); *A61B 2017/681* (2013.01)

(58) Field of Classification Search
CPC .............. A61B 17/708; A61B 17/7076; A61B 17/7077; A61B 17/7079; A61B 17/0206
See application file for complete search history.

(56) References Cited

U.S. PATENT DOCUMENTS

| 5,443,467 A * | 8/1995 | Biedermann ...... A61B 17/7037 606/65 |
| 8,906,034 B2 | 12/2014 | Gleeson et al. |

(Continued)

FOREIGN PATENT DOCUMENTS

| DE | 10 2015 120955 A1 | 6/2017 |
| DE | 10 2016 121054 B3 | 4/2018 |

(Continued)

OTHER PUBLICATIONS

Extended European Search Report for Application No. 18199467.4, dated Jul. 12, 2019, 12 pages.

*Primary Examiner* — Jan Christopher L Merene
(74) *Attorney, Agent, or Firm* — Lewis Roca Rothgerber Christie LLP

(57) ABSTRACT

A system for correcting a position of bones, bone parts, or vertebrae includes a first bone anchor including a shank for anchoring in bone and a receiver for connecting a rod to the shank, a second bone anchor including a shank for anchoring in bone and a receiver for connecting the rod to the shank, and an instrument including a positioning member, a first coupling member for coupling the positioning member to the first bone anchor, and a second coupling member for coupling the positioning member to the second bone anchor. The first and second coupling members are movable relative to one another. The receiver is pivotable relative to the shank for at least one bone anchor. The at least one bone anchor can assume a locked configuration where an angular position (Continued)

of the receiver relative to the shank is locked while the rod remains movable relative to the receiver.

25 Claims, 13 Drawing Sheets

(56) References Cited

U.S. PATENT DOCUMENTS

| | | | |
|---|---|---|---|
| 9,480,504 B1 | 11/2016 | Schafer et al. | |
| 2006/0084844 A1* | 4/2006 | Nehls | A61B 17/1757 600/227 |
| 2006/0200132 A1* | 9/2006 | Chao | A61B 17/7077 606/86 A |
| 2008/0125788 A1* | 5/2008 | Cohen | A61B 17/708 606/104 |
| 2010/0222644 A1* | 9/2010 | Sebastian | A61B 17/0206 600/228 |
| 2011/0077689 A1* | 3/2011 | Mickiewicz | A61B 17/7047 606/279 |
| 2011/0172714 A1* | 7/2011 | Boachie-Adjei | A61B 17/7076 606/264 |
| 2013/0289633 A1* | 10/2013 | Gleeson | A61B 17/708 606/86 A |
| 2015/0066088 A1* | 3/2015 | Brinkman | A61B 17/7077 606/264 |
| 2016/0000478 A1 | 1/2016 | Fischer et al. | |
| 2018/0055545 A1* | 3/2018 | Biedermann | A61B 17/7037 |
| 2018/0228520 A1* | 8/2018 | Bobbitt | A61B 17/025 |
| 2018/0271566 A1* | 9/2018 | Fischer | A61B 17/7079 |
| 2019/0231394 A1* | 8/2019 | Bechtel | A61B 17/025 |

FOREIGN PATENT DOCUMENTS

| | | |
|---|---|---|
| EP | 2 962 651 A1 | 1/2016 |
| EP | 3 287 088 A1 | 2/2018 |

* cited by examiner

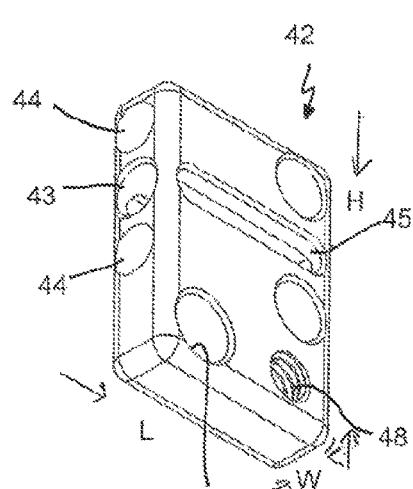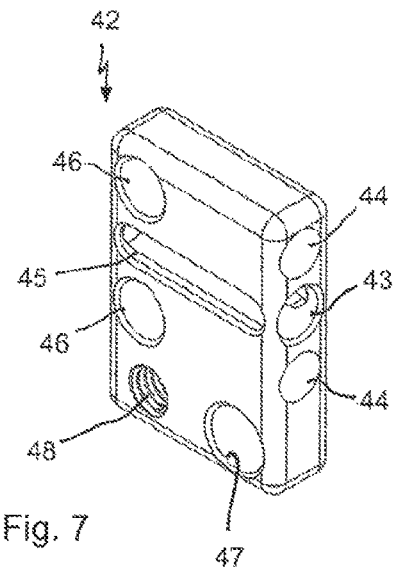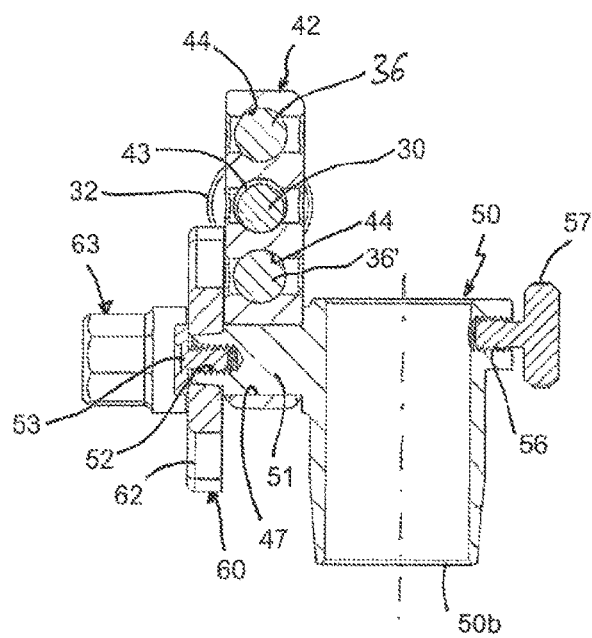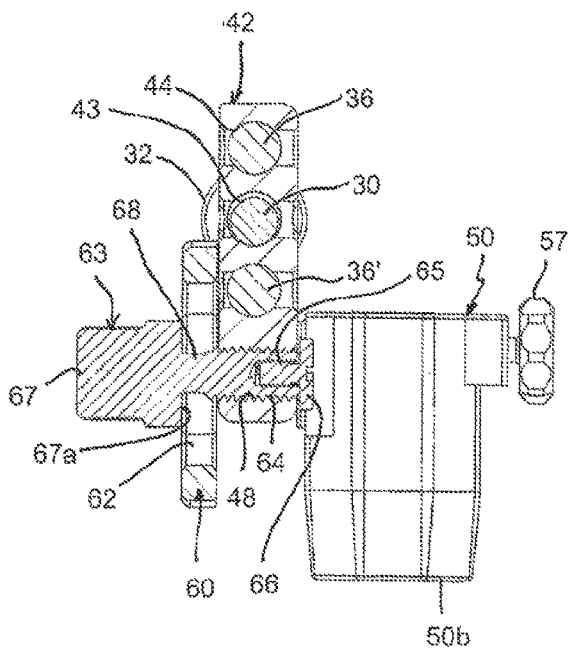

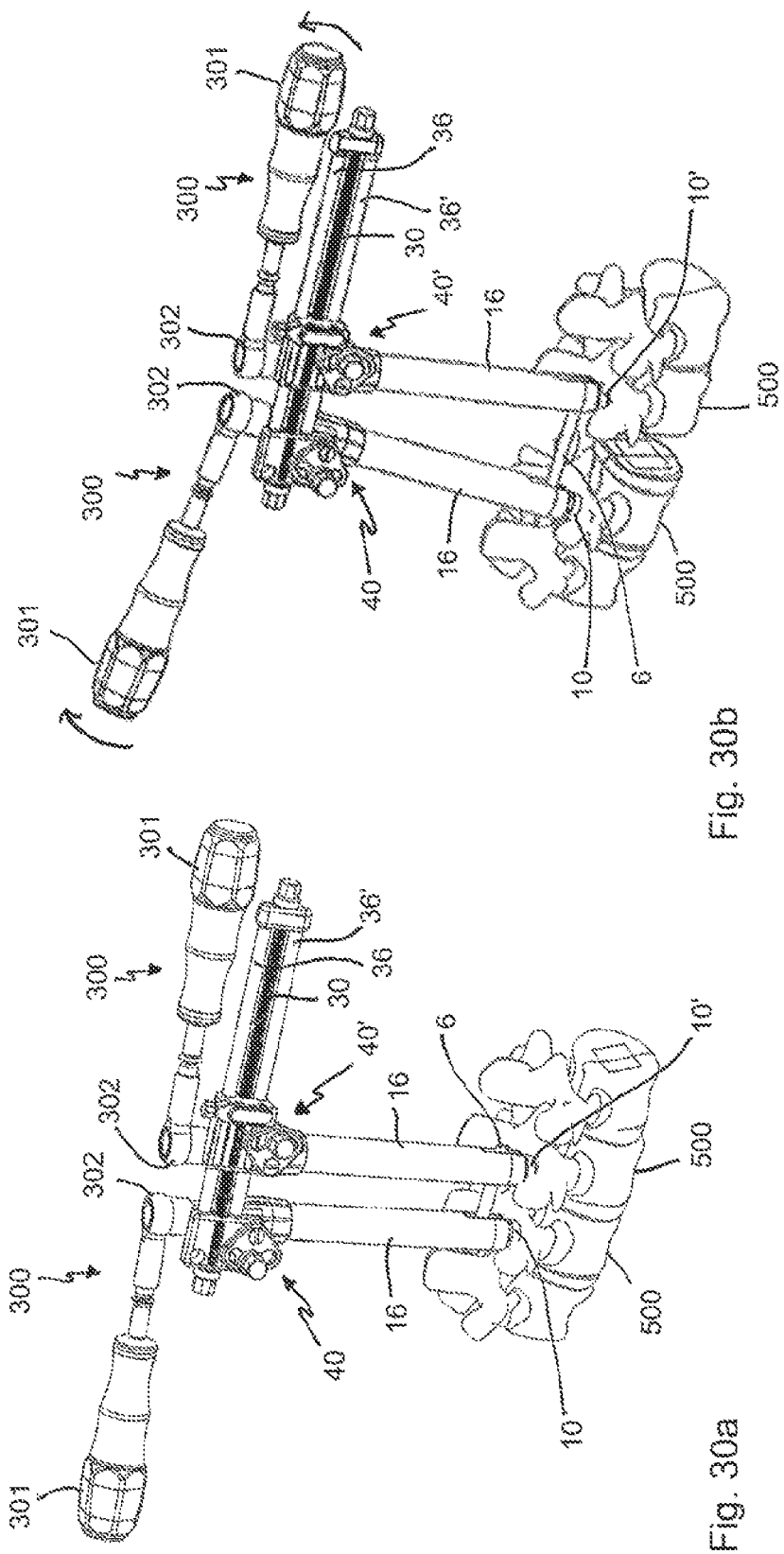

SYSTEM AND INSTRUMENT FOR CORRECTING A POSITION OF BONES, BONE PARTS, OR VERTEBRAE

CROSS-REFERENCE TO RELATED APPLICATION(S)

The present application claims priority to and the benefit of U.S. Provisional Patent Application No. 62/743,347, filed Oct. 9, 2018, the contents of which are hereby incorporated by reference in their entirety, and claims priority from European Patent Application EP 18 199 467.4, filed Oct. 9, 2018, the contents of which are hereby incorporated by reference in their entirety.

BACKGROUND

Field

The application relates to a system and an instrument for correcting a position of bones, bone parts, or vertebrae. More specifically, the application relates to a distraction and/or compression assembly, in particular for use in spinal and/or bone surgery.

Description of Related Art

Distraction and compression steps during spinal surgery are well-known in the art. For example, in the case of single or multilevel discectomies, cages, pedicle screws, and rods are often used for providing stability to the spinal segments. In order to remove the intervertebral disk and to insert a cage into the intervertebral space, the vertebrae are distracted. This is accomplished by using, for example, distraction pliers that engage two adjacent pedicle screws along a rod captured therein and that spread them apart from each other. Thereby, the intervertebral space is enlarged. During distraction, considerable loads may act onto the vertebrae. In some situations, unwanted loads may be detrimental to the anchoring of the pedicle screws in the bone.

U.S. Pat. No. 9,480,504 B1 describes a surgical alignment and distraction frame and associated methods of use that facilitate correction of a sagittal imbalance. The alignment frame comprises an elongated rack, a first coupler coupled to the rack, the first coupler including a first attachment ring sized to receive a screw extension instrument, and a second coupler coupled to the rack and including an attachment ring sized to receive a screw extension instrument. The first and second couplers are rotatable relative to the frame. The surgical alignment and distraction frame can be used by a surgeon to determine an appropriate surgical correction for a patient suffering from a spinal instability or deformity.

U.S. Pat. No. 8,906,034 B2 describes an orthopedic instrument for compression and distraction of bone segments that includes a first receiver, a second receiver, a positioner member, and a guide member. The first receiver includes a first receiver aperture that receives a first screw extender. The second receiver includes a second extender aperture that receives a second screw extender. The positioner member translates the second receiver relative to the first receiver to apply one of a compression and a distraction force on the screw extenders.

SUMMARY

While the instruments according to the prior art may be applicable in many clinical situations, there is still a need for a system and/or an instrument that opens a still further enlarged field of applications.

For example, a known method to treat kyphosis and/or lordosis uses monoaxial pedicle screws that are inserted into adjacent vertebrae and a curved rod. In some specific examples of the method, Schanz screws are applied. It may be difficult to use known distraction devices in the case of such a treatment.

In minimally invasive surgery (MIS) only small incisions are made, and therefore, the available space for the surgical manipulations is reduced. This may also be the case in other fields of spinal surgery, such as cervical spinal surgery or pediatric spinal surgery.

It is an object of the invention to provide a system and an instrument for correction of the position of bones, bone parts, or vertebrae, that can be employed in an enlarged field of applications.

According to embodiments of the invention, a system for correcting the position of bones, bone parts, or vertebrae includes a first bone anchor including a shank for anchoring in bone and a receiver for receiving a rod and for connecting the rod to the shank, a second bone anchor including a shank for anchoring in bone and a receiver for receiving the rod and for connecting the rod to the shank, a positioning member having a longitudinal axis, a first coupling member for coupling the positioning member to the first bone anchor, and a second coupling member for coupling the positioning member to the second bone anchor, wherein the second coupling member is movable relative to the first coupling member on the positioning member along the longitudinal axis, wherein at least the first bone anchor or the second bone anchor is configured to assume a first configuration in which the receiver is pivotable relative to the shank and a second configuration in which the receiver is locked relative to the shank at an angle, and wherein the first or the second bone anchor is configured to assume the second configuration irrespective of the presence and/or the position of the rod in the receiver.

In another aspect, the first or second bone anchor is configured to assume the second configuration by interaction with an instrument and/or interaction with the rod, and is configured to remain in the second configuration after removal of the interaction with the instrument and/or the interaction with the rod.

With the system, it is possible to connect the positioning member via the first and second coupling members to the first and second bone anchors, with a rod being still movable up and down in a rod receiving recess of the receivers. Hence, the angular position of the receivers relative to the shanks can be locked without the need to introduce or reduce the rod in the receivers before locking the respective angular positions. This opens various improved possibilities of corrections, in particular with regard to spinal surgery. For example, in a case of kyphosis or lordosis, the bone anchors can be inserted into adjacent vertebrae and the angular positions of the receivers relative to the shanks can be adjusted with the rod inserted but without the need of fixing the rod or maintaining the interaction with an instrument for locking the angular positions. The rod can still move up and down to some extent. Mounting of the first and second coupling members to the bone anchors is facilitated as the angular positions of the receivers relative to the shanks are adapted to the local geometry at the surgical site. The coupling members can then be moved relative to each other so as to correct the misalignment of the vertebrae relative to each other. Finally, the rod is fixed with a set screw and the positioning member is removed. Compared to the use of monoaxial bone screws, the procedure is considerably facilitated and the result of the correction is improved.

Another way of application is parallel distraction and/or compression of vertebrae. Maintaining the locking of the angular positions of the receivers relative to the shanks without the interaction with an instrument or without the interaction with the rod facilitates easier handling during surgery.

The system and the instrument is particularly useful in MIS, however, it can also be used for open surgery. The system and the instrument are not limited to use in spinal surgery, but can be used for any kind of bone surgery where it is necessary to correct the position of bones or bone parts relative to each other.

BRIEF DESCRIPTION OF THE DRAWINGS

Further features and advantages of the invention will become apparent from the description of embodiments by the aid of the accompanying drawings. In the drawings:

FIG. 6 shows a perspective view from the bottom of a first mounting portion of a first coupling member of the instrument of FIG. 5.

FIG. 7 shows a perspective view from the top of the mounting portion of FIG. 6.

FIG. 8 shows a cross-sectional view of the instrument of FIG. 5, wherein the cross-section is taken in a plane extending perpendicularly to a longitudinal axis of a positioning member and extending through the first mounting portion and a coupling portion.

FIG. 9 shows another cross-sectional view of the instrument in a plane perpendicular to the longitudinal axis of the positioning member and extending through the first mounting portion at another axial position along the longitudinal axis of the positioning member.

FIGS. 30a and 30b show steps of another exemplary use of an embodiment of the system.

DETAILED DESCRIPTION

Figure 1:
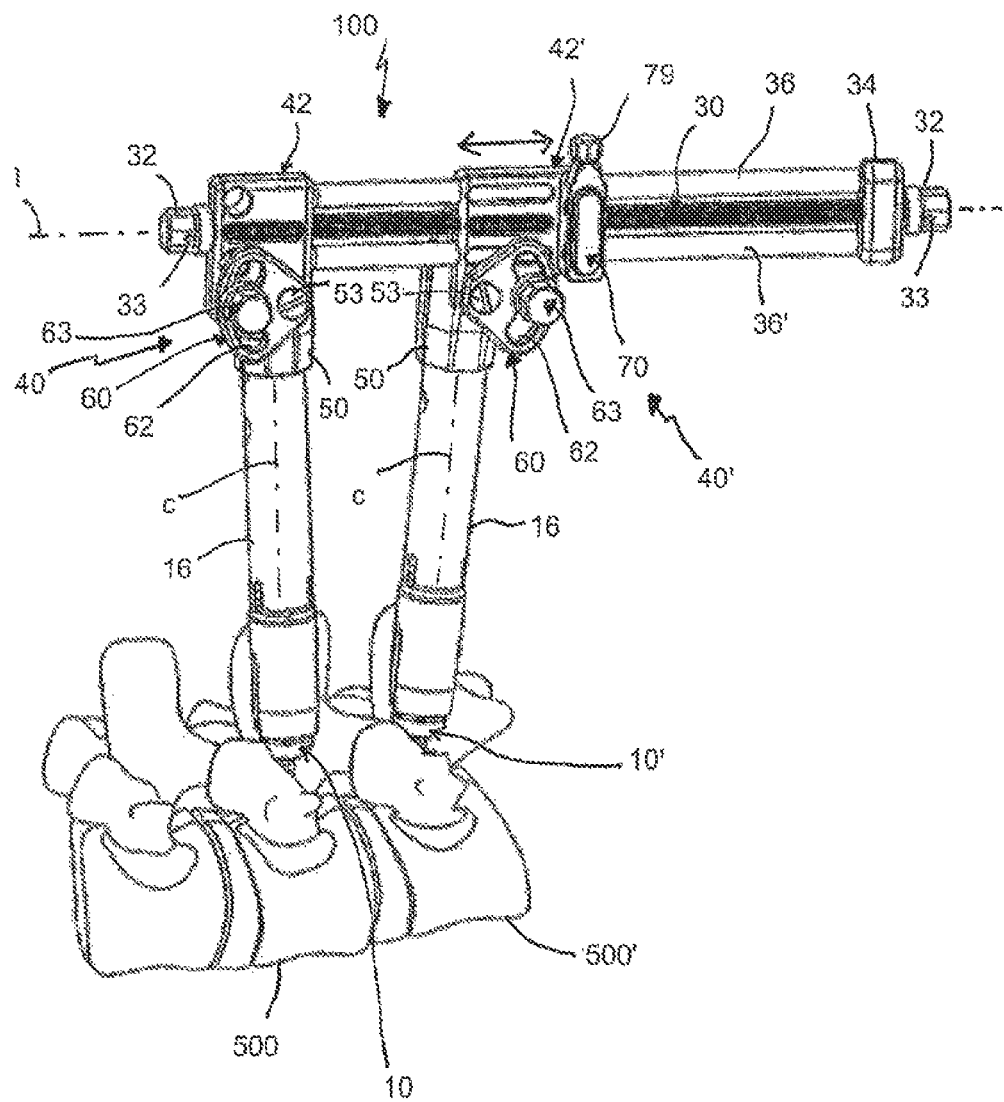
FIG. 1 shows a perspective view of a system for correcting the position of bones, bone parts, or vertebrae according to an embodiment of the invention.

Referring to FIG. 1, a system or assembly according to an embodiment comprises bone anchors 10, 10' and an instrument 100 connectable to the bone anchors 10, 10'. The bone anchors 10, 10' are configured to be inserted, for example, into the pedicles of adjacent vertebrae 500, 500'. However, the system can be employed with any other bones or bone parts in order to perform corrections of their respective positions.

Figure 2:
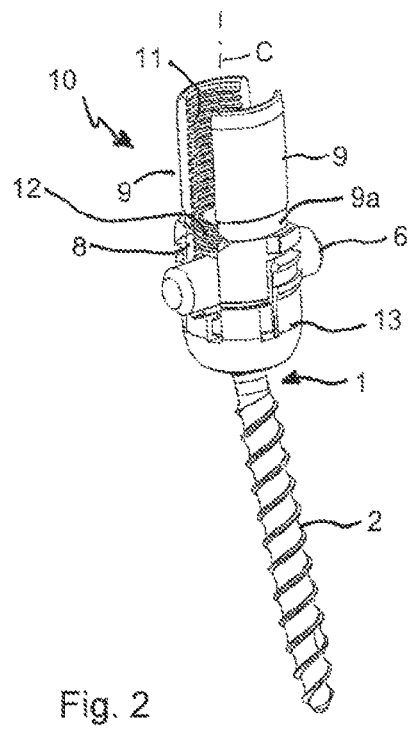
FIG. 2 shows a perspective view of an embodiment of a bone anchor of the system of FIG. 1.
Figures 3, 4:
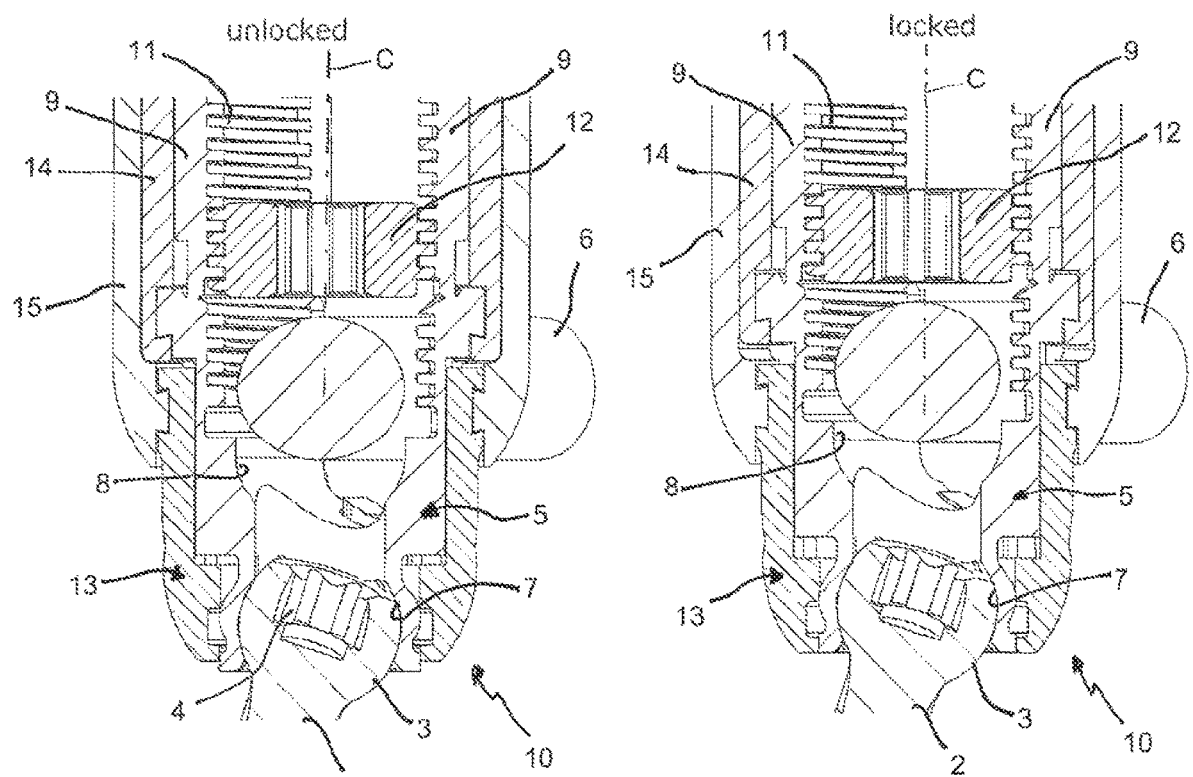
FIG. 3 shows a cross-sectional view of the bone anchor of FIG. 2, where a receiver of the bone anchor is in an unlocked state relative to a shank of the bone anchor, the cross-section taken through a plane including a central axis of the receiver and extending in a slanted manner relative to an axis of an inserted rod.
FIG. 4 shows a cross-sectional view of a portion of the bone anchor shown in FIG. 2 in a locked state of the receiver relative to the shank.

Referring now in more detail to FIGS. 2 to 4, an example of a bone anchor 10 that forms part of the system is described. The bone anchor 10 comprises an anchoring element 1 having a shank 2 that is configured to be anchored in bone. For example, the shank 2 may be partially threaded. Any other type of shank, for example nails, pins, etc., may be contemplated. At one end of the shank, a head 3 is formed that has a spherically shaped surface portion. Specifically, the head 3 may be formed as a spherical segment. At the free end of the head 3, an engagement structure 4 for a tool for screwing in the shank may be provided. The bone anchor 10 further includes a receiver 5 that is configured to accommodate the head 3 and to receive a rod 6, for example a spinal stabilization rod. To accomplish this, the receiver 5 comprises a head receiving portion 7 that may be expandable and compressible and that is configured to accommodate and pivotably hold therein the head 3. Further, the receiver 5 includes a rod-receiving recess 8 that is configured to receive the rod 6 therein. By means of the rod-receiving recess 8, two upstanding legs 9 are formed, the length of which may be such that they extend above an inserted rod 6 to such an extent that the rod 6 is able to move up and down in the recess 8. At an inner wall of the legs 9 an internal thread 11 may be provided to permit a fixation member 12, for example a fixation screw or set screw, to be inserted and tightened to fix the rod 6 within the receiver 5. The legs 9 may have a break-off section 9*a* that permits breaking off of a portion of the legs to reduce the height of the legs 9, for example, after the correction steps.

Around the head receiving portion 7, a locking ring 13 is arranged. The locking ring is configured to cooperate with the head receiving portion 7 in such a manner that in a first configuration that is shown in FIG. 3, the head receiving portion 7 is only slightly compressed, such that the head 3 is pivotable in the head receiving portion 7. Hence, in the first configuration, the shank 2 can assume various angular positions with respect to a central axis C of the receiver 5. In the first configuration, the head 3 may not be removed through a lower opening of the head receiving portion 7. In a second configuration, shown in FIG. 4, the locking ring 13 and the head receiving portion 7 are configured to cooperate in such a manner that the head receiving portion 7 is compressed such that the head 3 is locked in the head receiving portion 7. Hence, in the second configuration, the shank 2 assumes a fixed angle relative to the central axis C of the receiver.

Figure 28B:
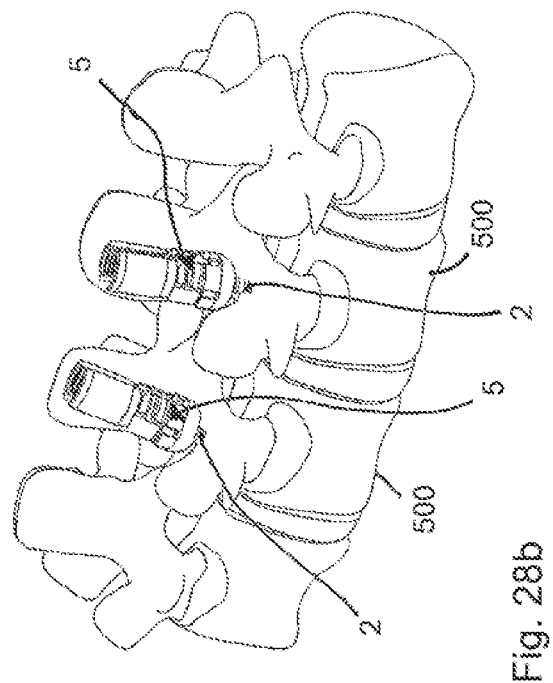
FIGS. 28a to 28e show steps of inserting bone anchors into adjacent vertebrae and of locking angular positions of the receivers relative to the shanks of the bone anchors according to an embodiment of the invention.
Figure 28A:
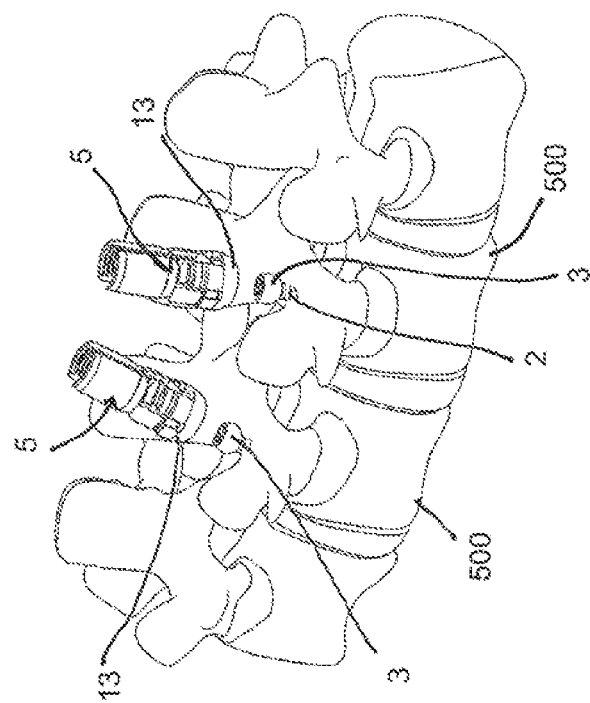
Figure 28E:
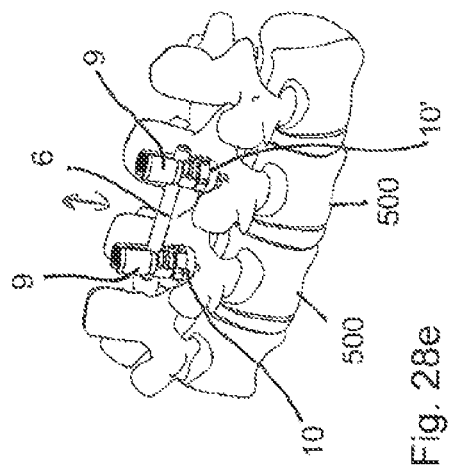
Figure 28D:
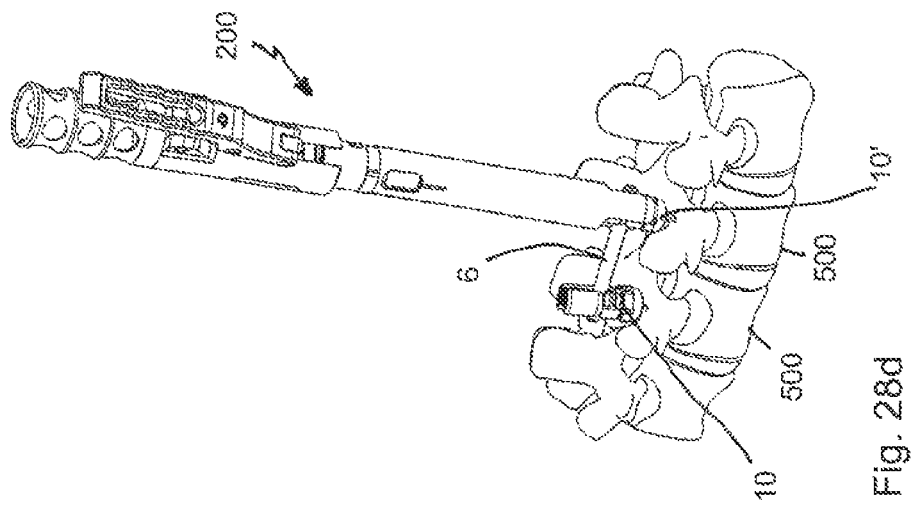
Figure 28C:
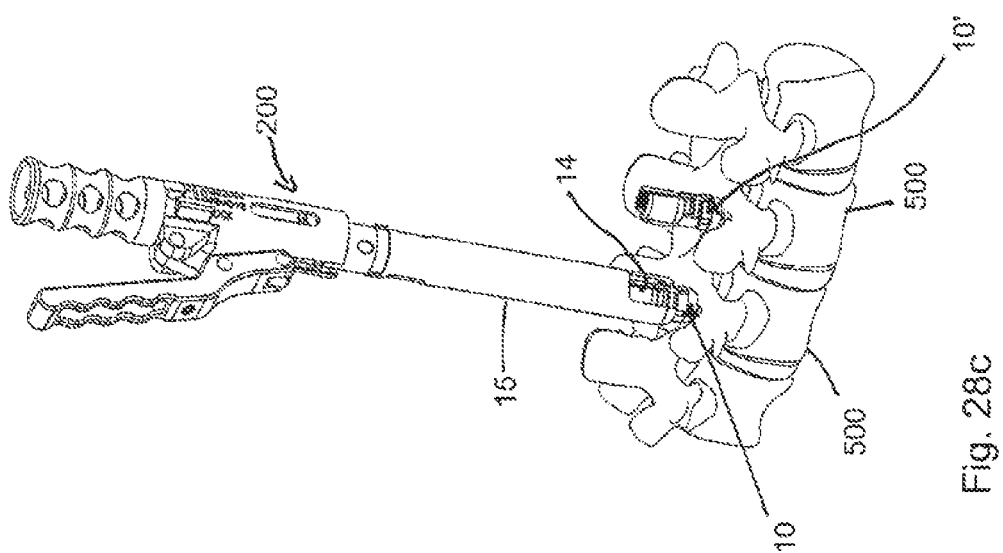

To change the bone anchor from the first configuration in which the receiver 5 is pivotable relative to the shank 2 to the second configuration in which the receiver 5 is locked relative to the shank 2, and vice versa, an instrument 200 may be used (see also, e.g., FIGS. 28*c* and 28*d*). The instrument may include a first or inner tubular portion 14 and a second or outer tubular portion 15, wherein the inner tubular portion 14 is configured to engage the receiver 5, preferably in the region of the legs 9, and the outer tubular portion 15 is configured to engage the locking ring 13. Relative displacement of the outer tubular portion 15 relative to the inner tubular portion 14 can move the locking ring 13 from the first configuration to the second configuration, and vice versa, thereby locking or unlocking the receiver 5 relative to the shank 2. The locking and unlocking may be effected by compressing and releasing the compression of the head receiving portion 7. The bone anchor 10 is configured to remain in the first configuration or in the second configuration, respectively, even after removal of the instrument. This may be achieved by frictional engagement of the locking ring 13 with the receiver 5, or by any releasable engagement structure between the locking ring and the receiver. It shall be noted, that the bone anchor 10 is configured to attain the second configuration in which the receiver is locked relative to the shank without using the rod 6 to lock the head.

The bone anchor depicted in FIGS. 2 to 4 is only an example of a bone anchor that is adapted to change between a first or unlocked configuration of the receiver relative to the shank and a second or locked configuration of the receiver relative to the shank without a rod being used to attain the second or locked configuration. More specifically, the bone anchor is adapted to assume the second configuration independent of the presence and/or the position of the rod in the receiver. Furthermore, the bone anchor may additionally be configured to remain in the locked or the unlocked configuration without an instrument holding the bone anchor in the locked or the unlocked configuration. Other types of bone anchors such as bone anchors having inner caps, top-loading and/or bottom-loading bone anchors, etc., may be used for the system, as long as the locked configuration can be maintained irrespective of the presence and/or the position of the rod in the receiver.

Turning now again to FIG. 1 and further to FIGS. 5 to 27, the instrument 100 will be described in detail. The instrument 100 includes a positioning member 30 having a first coupling member 40 and a second coupling member 40' mounted thereon. The positioning member 30 may be an elongate member having a longitudinal axis I. The first coupling member 40 and the second coupling member 40' are adapted to translate on the positioning member along the longitudinal axis I relative to each other, so that a distance between the first coupling member 40 and the second coupling member 40' may be varied. Each of the first coupling member 40 and the second coupling member 40' includes a sleeve-shaped coupling portion 50 that is adapted to be connectable to the bone anchor 10, 10'. For example, as shown in FIG. 1, the coupling portion 50 of each of the first and second coupling members 40, 40' is attached via a screw extender 16 or repositioning sleeve to the respective bone anchor 10, 10'. The coupling portions 50 define with their sleeve axis a coupling axis c. Each of the coupling portions 50 of the first and second coupling members 40, 40' is pivotably connected to the positioning member 30.

The positioning member 30 includes an advancement structure 31 on at least a part of its surface. The advancement structure 31 is configured to be engaged by an engagement portion of the second coupling member 40' so as to permit a relative translational movement of the first and second coupling members 40, 40' relative to each other in incremental steps. In more detail, the advancement structure 31 can be a thread and the positioning member 30 can be a threaded rod. On either end of the positioning member 30 an actuating member 32 is mounted that is configured to actuate the incremental advancement of the positioning member 30 relative to the second coupling member 40'. The actuating member 32 may be, for example, an actuating knob that is fixed to the positioning member 30 in a rotatably secured manner. For example, the actuating member 32 may have a threaded hole 32*a* so that it can engage the advancement structure 31 and can be secured by a transverse pin 33 or by any other rotatably secured connection, such as, for example, a press-fit connection. On one of the ends of the positioning member 30, a holding member 34 is provided that comprises an elongate through-hole 35, through which the positioning member 30 extends such that its one free end 30*a* projects out of the holding member 34 and is provided with or attached to the actuating member 32.

On the opposite end 30*b* the positioning member 30 is supported in a first mounting portion 42 of the first coupling member 40, such that it can rotate in an elongate through-hole 43 as explained in more detail below. Two guide members 36, 36' extend parallel to the positioning member 30 on opposite sides of the positioning member 30. The guide members 36, 36' may be implemented as rods, for example as rods having a smooth surface that facilitates sliding thereon. On their first ends 36*a*, 36'*a* the guide members are supported in holes 37 of the holding member 34 that are arranged on either side of the elongate through-hole 35, respectively. The ends 36*a*, 36'*a* of the guide members 36, 36', respectively, are fixed to the holding member 34, for example, by means of a press-fit connection. The opposite ends 36*b*, 36'*b* of the guide members 36, 36' are fixed to the first mounting portion 42, respectively. Thereby, the positioning member 30 and the guide members 36, 36' form a frame for holding and advancing the first and second coupling members 40, 40' relative to each other. The coupling portions 50 are pivotable in a plane spanned by or including their coupling axes c, which is parallel to a plane spanned by or including the longitudinal axis I of the positioning member 30 and the longitudinal axes of the guide members 36, 36'.

Turning now in more detail to FIGS. 5 to 9, the mounting of the first coupling member 40 on the positioning member 30 and on the guide members 36, 36' will be explained. In the embodiment, the first coupling member 40 remains translationally stationary with respect to the positioning member 30 and the guide members 36, 36'. The first mounting portion 42 of the first coupling member 40 may be formed as a substantially rectangular block having a length L in a direction parallel to the longitudinal axis I of the positioning member 30, a width W perpendicular to the longitudinal axis I and also perpendicular to the longitudinal axes of the guide members 36, 36', and a height H. Preferably the width W is smaller than the length L. Also, the height H may be greater than the width W. Such a shape may contribute to a compact size of the instrument 100. The elongate through-hole 43 extends throughout the length L of the first mounting portion 42 and is located in the height direction above the middle of the mounting portion 42. Above and below the through-hole 43, in the height direction, two guide member receiving holes 44 are formed that are shaped and sized so as to firmly receive the ends 36b, 36'b of the guide members 36, 36' therein. The guide member receiving holes 44 may not extend throughout the length L of the first mounting portion 42.

Along the elongate through-hole 43 through which the positioning member 30 passes, there are elongate holes 45 in the surface of the first mounting portion 42 that extend parallel to the elongate through-hole 43 and enable viewing of the positioning member 30 running through the through-hole 43. At an opposite side of the guide member receiving holes 44, two transverse through-holes 46 may be provided in the first mounting portion 42 that are above and below the positioning member receiving through-hole 43 and that may serve for reducing the weight and/or facilitating cleaning, for example.

In the lower portion of the first mounting portion 42 in the height direction, i.e., below the lower guide member receiving hole 44, in a region close to the corner, there is a coupling portion receiving hole 47 that extends transversely across the first mounting portion 42 in the width direction. The coupling portion receiving hole 47 is configured to receive therein a pivot arm 51 of the coupling portion 50 that extends perpendicularly to the coupling axis c. The pivot arm 51 is adapted to rotate in the coupling portion receiving hole 47, so as to permit the adjustment of an angle of the coupling portion 50 relative to the positioning member 30. At approximately the same height position as the coupling portion receiving hole 47, close to the opposite corner, a fixation member receiving hole 48 is provided that may, for example, be threaded to receive therein a threaded pin for fixing a pivot position of the coupling portion 50 as described in more detail below.

Next, the coupling portion 50 will be described with additional reference to FIGS. 10 to 13. The coupling portion 50 can be identical for both the first and second coupling members 40, 40'. The coupling portion 50 is sleeve-shaped and has an upper end 50a and an opposite lower end 50b. Close to the upper end 50a, the pivot arm 51 extends transversely to the coupling axis c. The pivot arm 51 is configured to be received in the coupling portion receiving hole, for example, of the first mounting portion 42, in a rotatable manner. At an outer free end of the pivot arm 51, a threaded blind hole 52 is provided that is configured to receive a fixation screw 53 that attaches the coupling portion 50 to the first mounting portion 42, as shown, for example, in FIGS. 5 and 8. A mounting structure 54, such as a tapered square-end structure, is formed at a free end of the pivot arm 51. Such a mounting structure 54 may serve for mounting a pivot position fixing plate 60, as shown for example in FIG. 8, to the pivot arm 51 in an oriented manner. Adjacent or close to the upper end 50a, the coupling portion 50 further comprises at a side opposite to the pivot arm 51 a projection 55 that includes a fixation member receiving hole 56, for example a threaded hole, which extends perpendicularly to the coupling axis c. The fixation member receiving hole 56 receives a fixation member 57, for example, a fixation screw (FIG. 5) therein for fixing the coupling portion to the screw extender 16. An inner diameter of the coupling portion 50 is sized such that the screw extender 16 can pass therethrough and can be clamped by the fixation member 57. An outer shape of the coupling portion 50 may be polygonal, but it can also be cylindrical. Moreover, the outer surface may slightly taper towards the lower end 50b. Such a design may reduce the overall weight of the coupling portion 50 and contribute to a compact size.

It shall be noted that a length 51a of the pivot arm 51 that extends between a thickened wall portion 58 and the mounting structure 54 corresponds approximately to the width W of the first mounting portion 42 as can be seen, for example, in FIG. 8.

The coupling portion 50 for the first coupling member 40 can be identical to the coupling portion 50 of the second coupling member 40'.

Next, the pivot position fixing plate 60 will be explained in more detail with reference to FIGS. 5, 8, and 9. The pivot position fixing plate 60 is substantially plate-shaped, with a thickness corresponding to or being only slightly greater than the axial length of the mounting structure 54 of the pivot arm 51. An outer contour of the pivot position fixing plate 60 may be substantially circle segment-shaped, with a flat end 60a opposite to a curved end 60b. Close to the flat end 60a, there is a transverse through-hole 61 that extends completely through the plate 60. An inner contour of the through-hole 61 corresponds to an outer contour of the mounting structure 54 of the pivot arm 51. In the example shown, the through-hole 61 has a four-cornered contour like the mounting structure 54 of the pivot arm 51. Hence, the pivot position fixing plate 60 can be mounted in such a manner that the curved end 60b can generally point in a direction parallel to the longitudinal axis I, either to the left or to the right. For the first coupling member 40, the curved end 60b points in the same direction as the second end 30b of the positioning member 30. Further, a curved elongate through-hole 62 is provided in the pivot position fixing plate 60 at a distance from the curved end 60b, and comprises a curvature that may correspond to the curvature of the curved end 60b. The curved through-hole 62 forms a pivot angle limiting structure that is configured to limit the range of pivoting of the coupling portion 50. Hence, the outer ends 62a, 62b of the curved through-hole 62 form stops, respectively, for limiting the pivot angle of the coupling portion 50 relative to the positioning member 30.

A pivot position fixing member 63 is adapted to fix a pivot angle of the coupling portion 50 relative to the positioning member 30 at any pivot angle between the maximum pivot angles defined by the ends 62a, 62b of the curved elongate through-hole 62. The pivot angle position fixing member 63 comprises a threaded pin portion 64 that has a length adapted to extend through the fixation member receiving hole 48 of the first mounting portion 42 as depicted in FIG. 9 (the same or a similar pivot angle position fixing member 63 can be used similarly with the second mounting portion 42', as described in greater detail below). At its free end, the threaded pin 64 comprises a threaded hole 65 to receive a fixation screw 66 (FIGS. 5 and 9) therein. On the side opposite to the threaded hole 65, an actuating portion 67 is formed that may be, for example, a knob with a polygonal outer structure that facilitates gripping and rotating of the knob. Between the threaded pin 64 and the actuating portion 67, a thread-free neck portion 68 may be formed. An outer diameter of the neck portion 68 and the threaded pin portion 64 is such that they can extend through the curved elongate through-hole 62 of the pivot position fixing plate 60 and permit the pivot position fixing plate 60 to move relative to the neck portion 68. A surface 67a of the actuating portion 67 that faces the direction of the neck portion 68 has a width that is greater than a transverse width of the curved elongate through-hole 62. As shown in FIG. 9, when the coupling portion 50 and the pivot position fixing plate 60 are mounted to the first mounting portion 42, the threaded pin portion 64 extends through the fixation member receiving hole 48 of the first mounting portion 42 and is engaged by the fixation screw 66. The pivot position fixing plate 60 is sandwiched between the actuating portion 67 and the first mounting portion 42.

Figure 26:
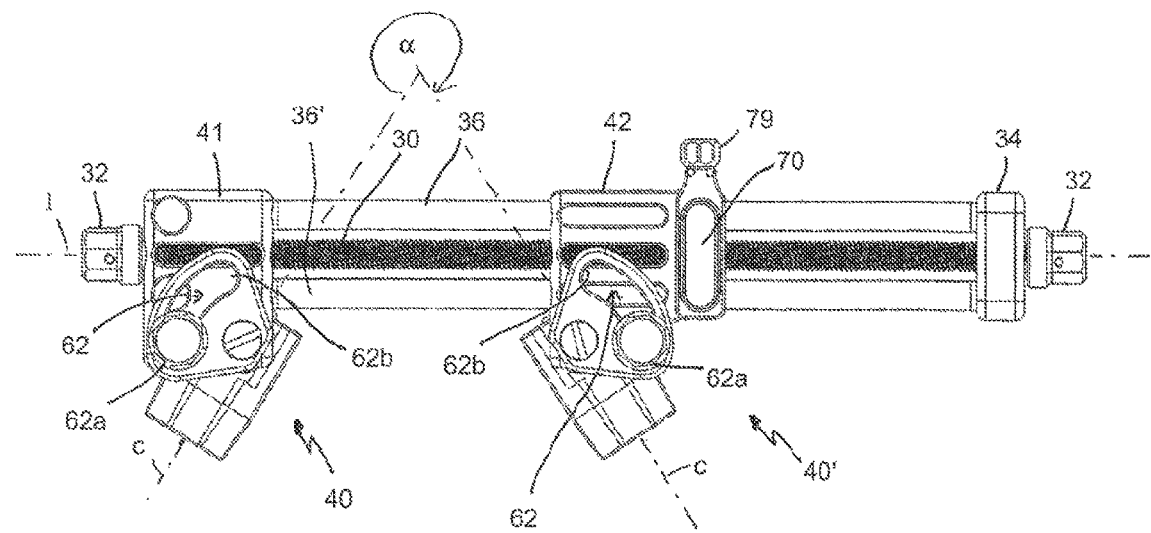
FIG. 26 shows a side view of the instrument of FIGS. 5, 24, and 25 with the first and second coupling members of the instrument in one pivot position.
Figure 27:
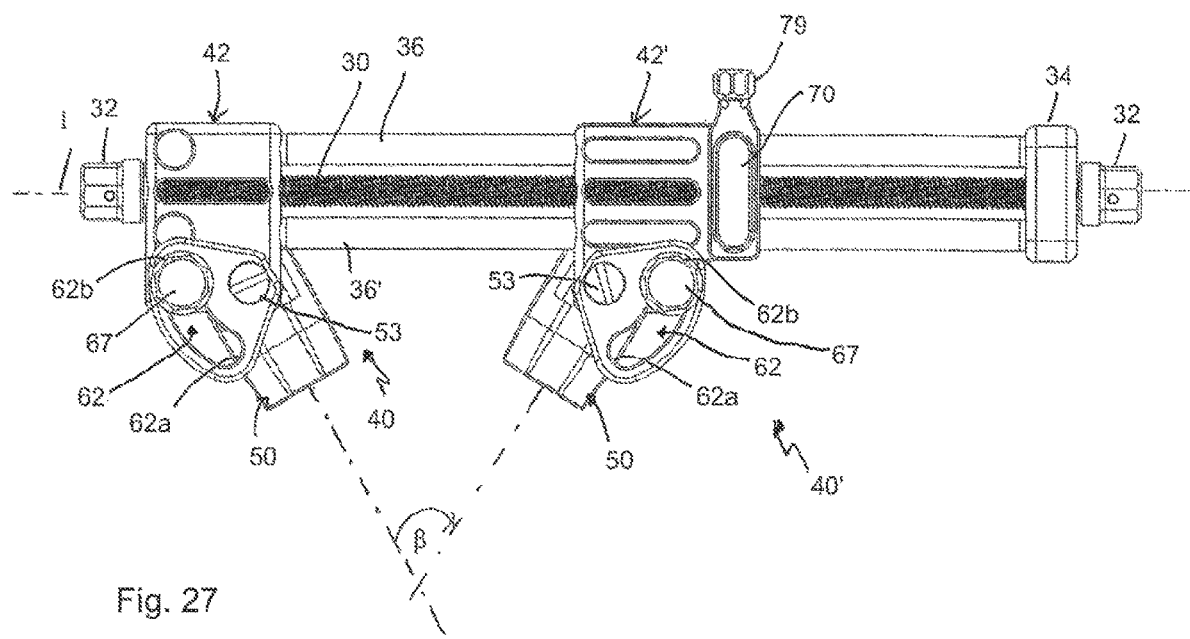
FIG. 27 shows a side view of the instrument with the first and second coupling members in another pivot position.

The mounting and function of the first coupling member 40 to the positioning member 30 and the guide members 36, 36' is as follows. The positioning member 30 extends through the elongate through-hole 43 of the first mounting portion 42, such that the second end 30b projects out of the first mounting portion 42 and is provided with the actuating member 32. The guide members 36, 36' are fixed to the guide member receiving holes 44 of the first mounting portion 42. Hence, the first coupling member 40 is translationally fixed relative to the positioning member 30 and the guide members 36, 36'. The coupling portion 50 is mounted in a pivotable manner to the first mounting portion 42 via the pivot arm 51 extending through the coupling portion receiving hole 47. The pivot position fixing plate 60 is oriented such that the elongate through-hole 62 is between the pivot arm 51 and the outer end of the first mounting portion 42 facing towards the actuating member 32. Turning the actuating portion 67 of the pivot position fixing member 63 in one direction increases the distance between the surface 67a and the first mounting portion 42, so that the coupling portion 50 is pivotable around the axis of the pivot arm 51. Pivoting the coupling portion 50 also pivots the pivot position fixing plate 60 that is fixed to the pivot arm 51. As shown in FIGS. 26 and 27, the pivoting is limited by the pivot angle limiting structure, in the form of the curved elongate through-hole 62, when the neck portion 68 or the threaded pin portion 64 abuts against the ends 62a or 62b as shown in FIGS. 26, 27, respectively. The pivot position of the coupling portion 50 can be fixed at any position between the limits by rotating the actuating portion 67 in the opposite direction, thereby clamping the pivot position fixing plate 60 between the surface 67a of the actuating portion 67 and the first mounting portion 42.

Next, the second coupling member 40' and the mounting thereof will be described. The pivoting mechanism of the coupling portion 50 of the second coupling member 40' is the same as for or similar to that of the first coupling member 40. However, the pivot position fixing plate 60 is mounted such that the elongate curved through-hole 62 is between the pivot arm 51 and the side of the instrument 100 where the first end 30a of the positioning member 30 is located.

Figure 25:
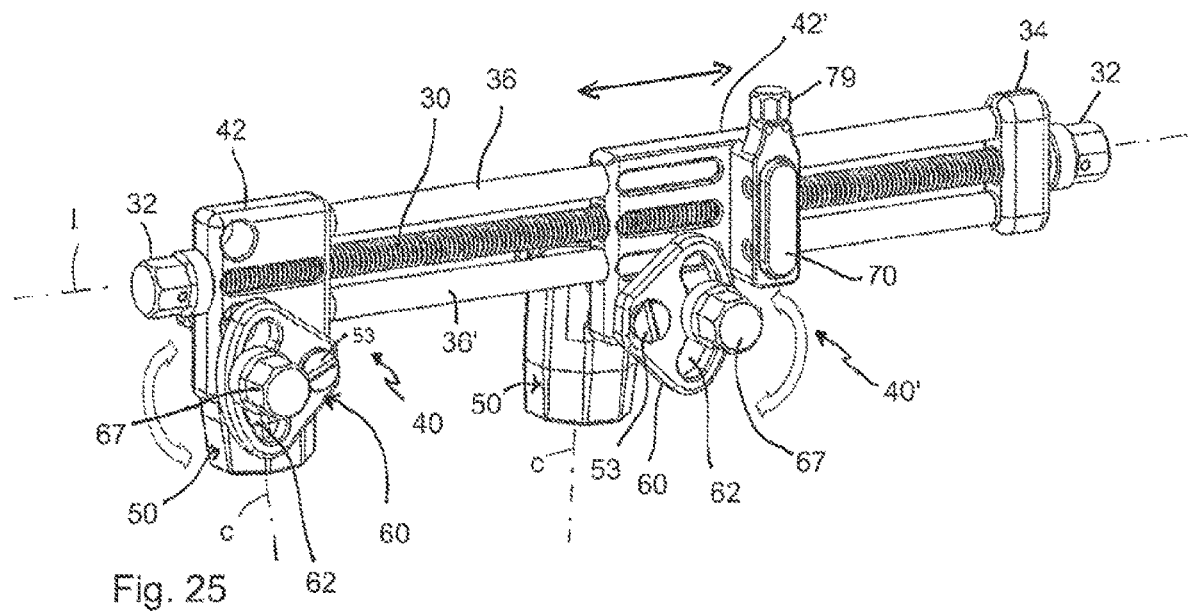
FIG. 25 shows a perspective view of the instrument from an opposite side of the view shown in FIG. 24.

The second mounting portion 42' will be described in more detail with reference to FIGS. 14 to 19. The second mounting portion 42' comprises a main mounting body 41 that is similar to the first mounting portion 42 of the first coupling member 40. It has a substantially rectangular block shape with a length L parallel to the longitudinal axis I of the positioning member 30, a width W perpendicular to the longitudinal axis I that is smaller than the length L, and a height H in a direction perpendicular to the positioning member 30 and the guide members 36, 36', the height H also being greater than the width W. An elongate through-hole 43' located in an upper half of the second mounting portion 42' in the height direction is provided for guiding through of the positioning member 30. Above and below the through-hole 43', elongate guide member receiving through-holes 44' are provided for guiding through of the guide members 36, 36', respectively. Different from the first mounting portion 42, the guide member receiving through-holes 44' extend fully from one side to the other side of the second mounting portion 42', and are sized such that the guide members can slide therein in the lengthwise direction. Corresponding to the position member receiving through-hole 43' and the guide member receiving through-holes 44', elongate through-holes 45', 46' are provided that pass through the main body 41 in the widthwise direction, respectively. Below the lower one of the guide member receiving through-holes 44', there are formed a coupling portion receiving hole 47' close to one corner that receives the pivot axis 51 of the coupling portion 50, and a fixation member receiving hole 48' for receiving the threaded pin portion 64 of the actuating member 63 close to the opposite corner. The second mounting portion 42' is mounted to the positioning member 30 and the guide members 36, 36' in such a manner that the coupling portion receiving hole 47' is on the side positioned closer to the first coupling member 40 (FIGS. 5 and 25).

Figure 17:
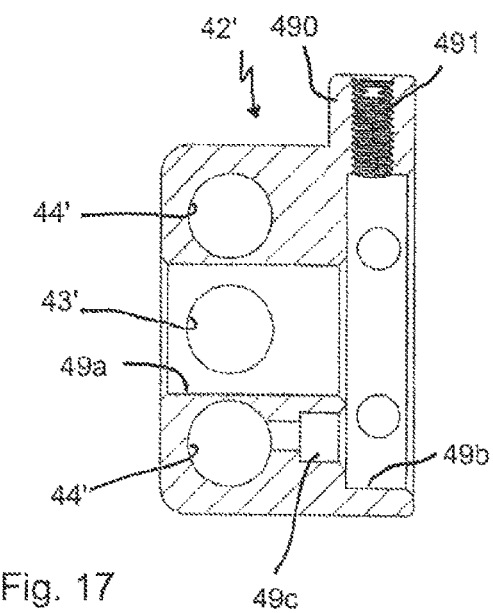
FIG. 17 shows a cross-sectional view of the second mounting portion of FIGS. 14 to 16, the cross-section taken in a plane indicated with arrows A-A in FIG. 14.
Figure 18:
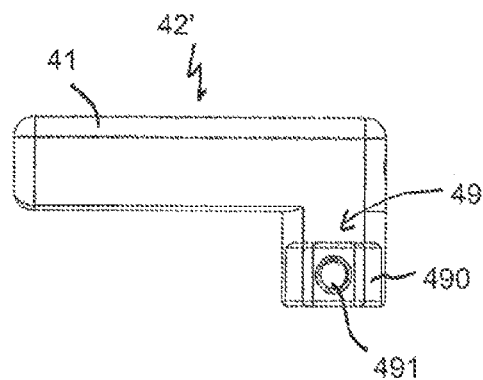
FIG. 18 shows a top view of the second mounting portion of FIGS. 14 to 17.
Figure 19:
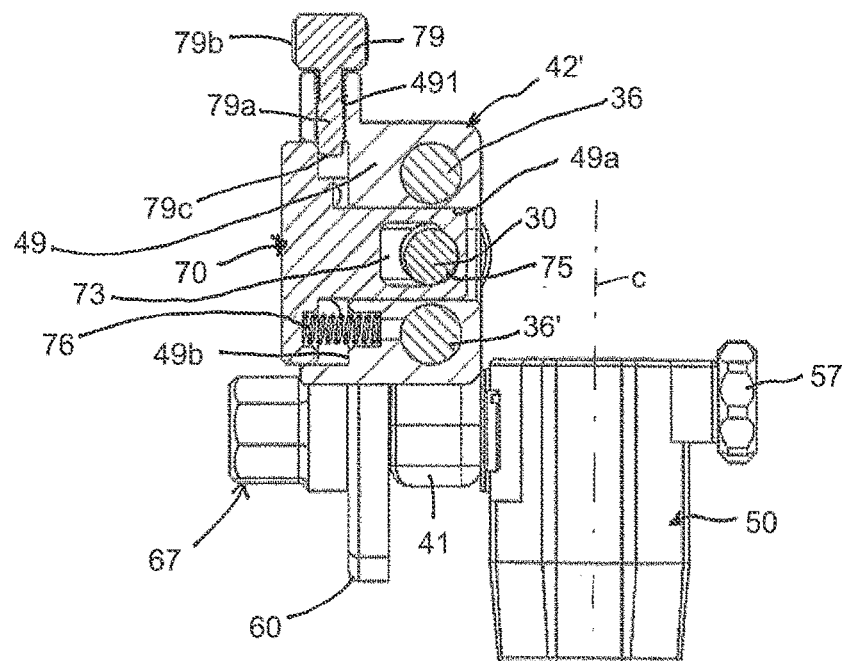
FIG. 19 shows a cross-sectional view of the instrument of FIG. 5 in a plane extending perpendicularly to the longitudinal axis of the positioning member and through the second mounting portion of FIGS. 14 to 18.
Figure 20:
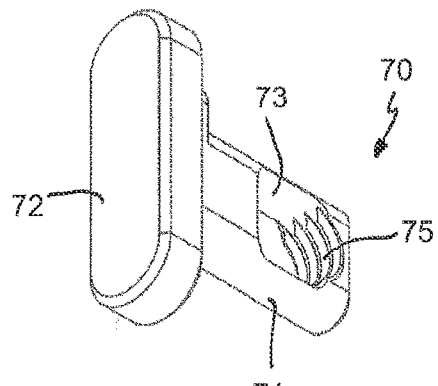
FIG. 20 shows a perspective view from one side of an actuating member for actuating translational movement of the second coupling member of the instrument of FIG. 5.

Adjacent to the side where the fixation member receiving hole 48' is located, the second mounting portion 42' comprises an extension 49 from the main body 41 which extends at a substantially right angle away from the main body and is offset from the fixation member receiving hole 48' in the height direction. The extension 49 forms a housing for a translation movement actuating mechanism. The translation movement actuating mechanism is configured to permit an incremental translational movement of the second coupling member 40' relative to the positioning member 30 in a first operating configuration. Furthermore, the translation movement actuating mechanism is configured to permit a sliding translational movement of the second coupling member 40' relative to the positioning member 30 in a second operating configuration. As depicted in FIG. 17, the positioning member receiving through-hole 43' and the guide member receiving through-holes 44' extend through the extension 49. Moreover, the extension 49 comprises a first elongate recess 49a at the height of the position member receiving through-hole 43', wherein a long side of the recess 49a extends in the height direction. Adjacent to the first elongate recess 49a, a second larger elongate recess 49b is formed. The smaller elongate recess 49a is oriented in a mounted state toward the coupling portion 50, and the larger elongate recess 49b is oriented towards the opposite side (FIG. 19). In addition, on the side of the lower guide member receiving through-hole 44', there is a recess 49c for accommodating therein a biasing member, for example a helical spring, as explained below. At a free end of the extension 49 a protrusion 490 is formed that is provided with a threaded through-hole 491 to receive a locking member therein.

The translation movement actuating mechanism will now be described in more detail, referring to FIG. 19 to 23. The translation movement actuating mechanism includes an actuating button 70. The actuating button 70 comprises a first elongate portion 71 with an elongate shape, the outer contour of which is designed to fit into the first recess 49a of the extension 49, and is able to slide therein in a direction perpendicular to the longitudinal axis I of the positioning member 30. Adjacent to the first elongate portion 71, there is a second elongate portion 72 extending transversely to the first elongate portion. The second elongate portion 72 forms a push portion and has an outer contour such that it fits into the larger second recess 49b of the extension 49. Adjacent to a free end 71a of the elongate first portion 71, there is a rectangular or square-shaped transverse recess 73 that extends completely through the elongate first portion 71 from one long side to the other long side. On one side of the recess 73 that is closer to the free end 71a, a cylinder segment-shaped recess 74 is formed, the cylinder axis of which extends parallel to the longitudinal axis I of the positioning member 30 or coincides with the longitudinal axis I when the actuating button 70 is mounted to the second mounting portion 42'. An advancement structure 75, which may be a thread that is configured to cooperate with the advancement structure 31 of the positioning member 30, is formed in the cylindrical recess 74. The actuating button 70 has a size such that, when it is inserted into the first and second recesses 49a, 49b of the extension 49, the advancement structure 75 is at a position where it is permitted to engage the advancement structure 31 of the positioning member 30, as shown in FIG. 19. In the first operating configuration, the advancement structure 75 of the button 70 and the advancement structure 31 of the positioning member 30 are engaged. To maintain the first operating configuration, a biasing member 76 in the form of, for example, a helical spring, is inserted into the recess 49c in such a manner that it extends into a corresponding circular recess 77 at the side of the second portion 72 of the actuating button 70 that faces in the direction of the first portion 71. Therefore, as shown in FIG. 19, in the first operating configuration, the biasing member 76 pushes the actuating button 70 outward, so that the advancement structure 75 of the actuating button 70 and the advancement structure 31 of the positioning member 30 remain engaged.

With the biasing member 76, the actuating button 70 is held in the first operating configuration. Hence, rotating the positioning member 30 by actuating either one of the actuating members 32 incrementally moves the second mounting portion 42' relative to the positioning member 30, thereby varying the distance between the first coupling member 40 and the second coupling member 40' in an incremental manner corresponding to the increments of the advancement structures 75, 31.

Figure 21:
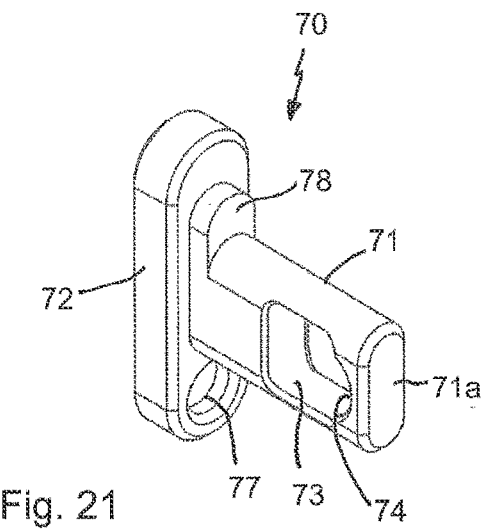
FIG. 21 shows a perspective view of the actuating member of FIG. 20 from another side.
Figure 22:
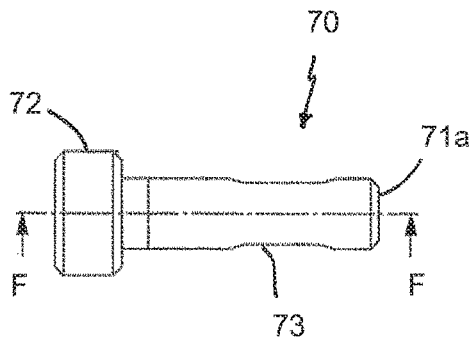
FIG. 22 shows a top view of the actuating member of FIGS. 20 and 21.
Figure 23:
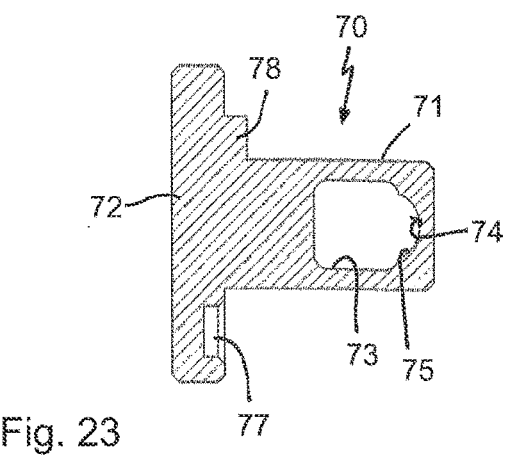
FIG. 23 shows a cross-sectional view of the actuating member of FIGS. 20 to 22, the cross-section taken along line F-F in FIG. 22.
Figure 24:
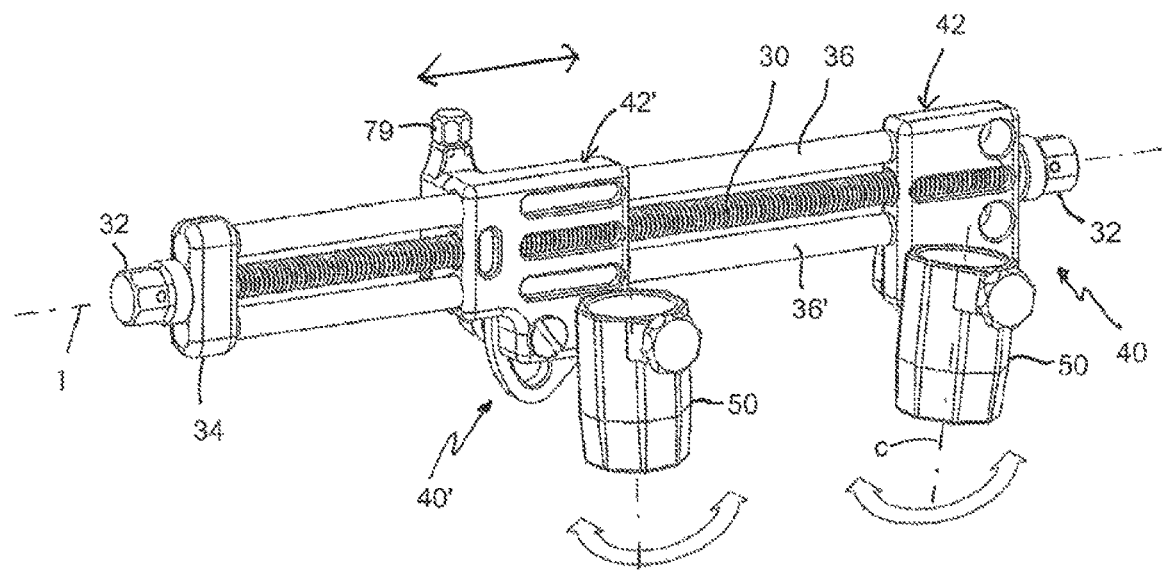
FIG. 24 shows a perspective view of the instrument of FIG. 5 from one side.

As can be further seen, for example, in FIGS. 21 and 23, between the first elongate portion 71 and the second elongate portion 72, a step-like projection 78 that has a shape corresponding to the rounded shape of the end portions of the elongate portions 71, 72 may be formed. The step portion 78 may have, for example, a function of facilitating the orientation of the button 70 when mounting the button 70, or a function of limiting the insertion path of the actuating button 70.

Figure 5:
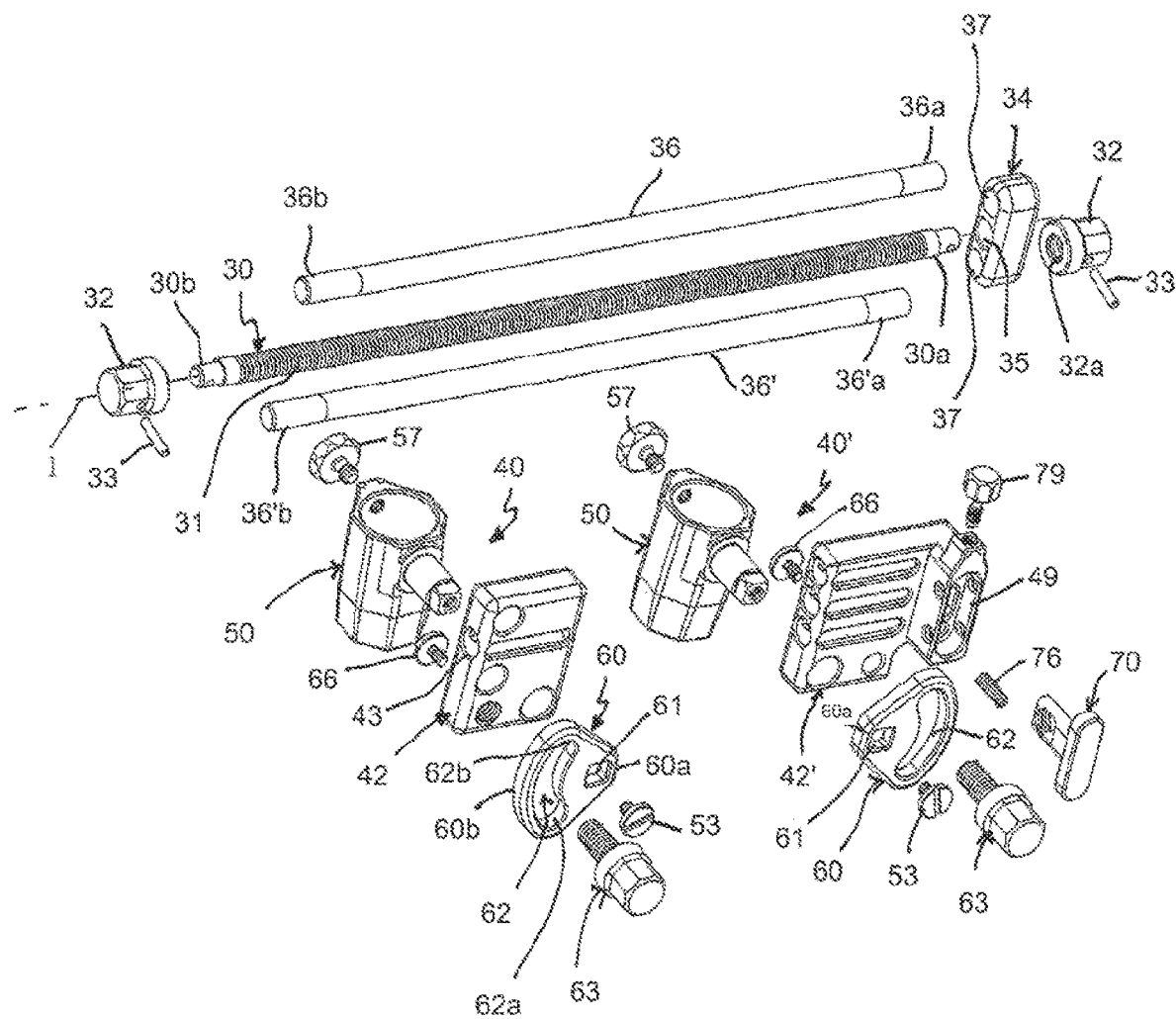
FIG. 5 shows an exploded perspective view of a first embodiment of an instrument that forms a system together with the bone anchor of FIGS. 2 to 4 according to one embodiment of the invention.
Figure 10:
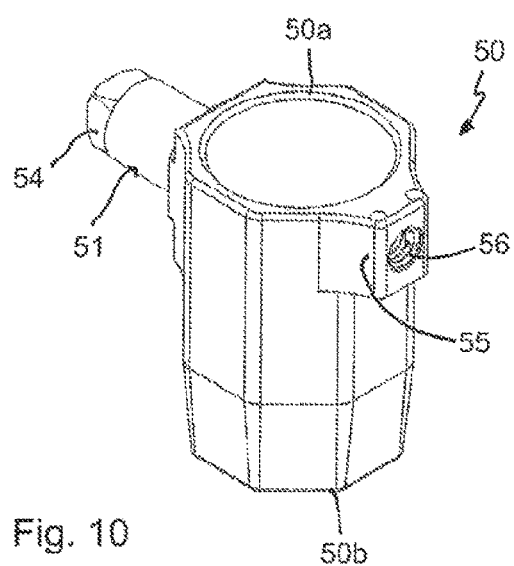
FIG. 10 shows a perspective view from the top of the coupling portion of a coupling member of the instrument of FIG. 5
Figure 11:
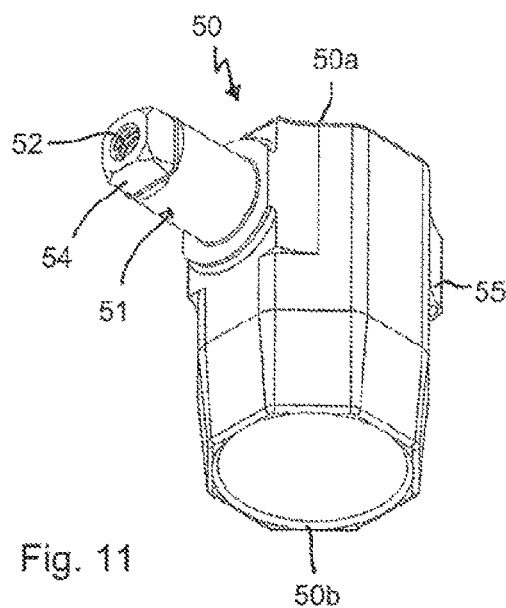
FIG. 11 shows a perspective view from the bottom of the coupling portion of FIG. 10.
Figure 12:
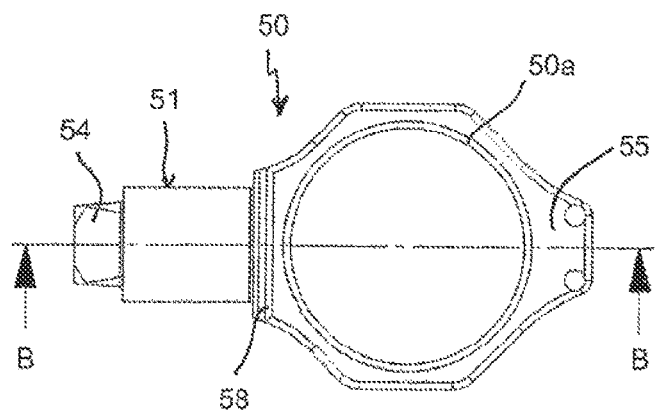
FIG. 12 shows a top view of the coupling portion of FIGS. 10 and 11.
Figure 13:
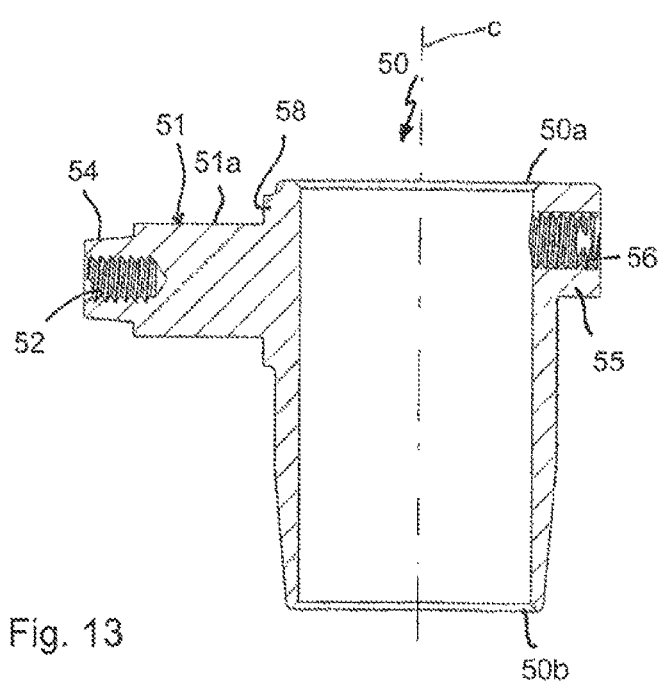
FIG. 13 shows a cross-sectional view of the coupling portion of FIGS. 10 to 12, the cross-section taken along line B-B in FIG. 12.
Figure 14:
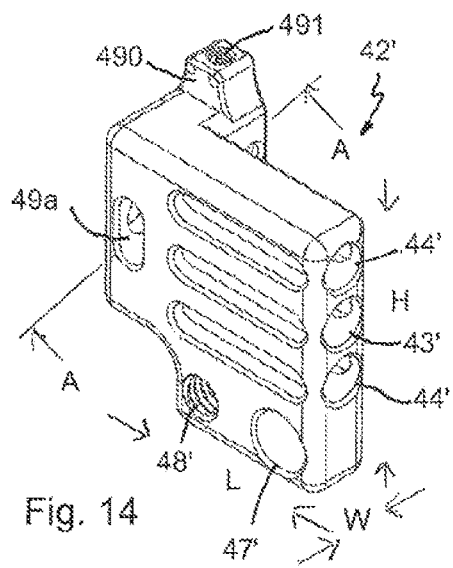
FIG. 14 shows a perspective view from the top of a second mounting portion of a second coupling member of the instrument of FIG. 5.
Figure 15:
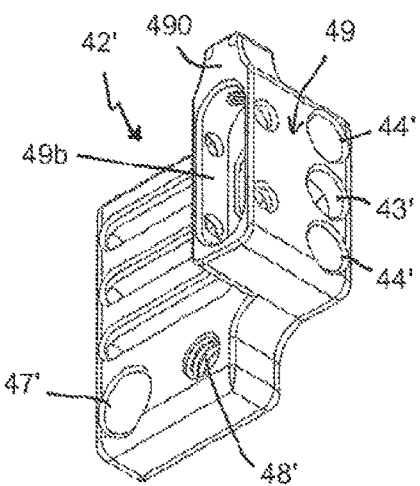
FIG. 15 shows a perspective view from the bottom of the second mounting portion of FIG. 14.
Figure 16:
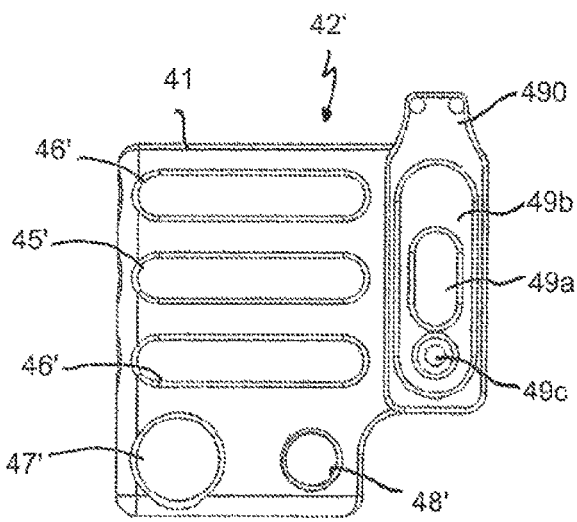
FIG. 16 shows a side view of the second mounting portion of FIGS. 14 and 15.

Turning now to FIGS. 5 and 19, the first operating configuration can be secured by applying a securing member 79. The securing member 79 may be in the form of a securing screw that has a threaded shaft 79a with a length such that it can extend completely through the threaded hole 491 of the extension 49. The securing member 79 may also have a head 79b with a larger diameter than the shaft 79a so that, when the securing member 79 is completely tightened, a free end portion 79c extends into the second recess 49b and blocks the actuating button 70 from being pushed against the force of the biasing member 76.

To release the engagement between the advancement structure 75 of the actuating button 70 and the advancement structure 31 of the positioning member 30, the securing member 79 is loosened until the threaded shaft 79a no longer blocks the actuating button 70. By means of this, the actuating button 70 can be pushed in a direction transverse to the longitudinal axis I of the positioning member 30 against the biasing force of the biasing member 76, with the result that the first portion 71 of the actuating button 70 moves deeper into the first recess 49a and disengages the positioning member 30 from the advancement structure 75. When the advancement structures 75, 31 are disengaged, the second coupling member 40' is in the second operating configuration, in which it can be slidingly translated on the positioning member 30 and the guide members 36, 36'. The second operating configuration serves to facilitate a quick displacement of the first and the second coupling members 40, 40' relative to each other. When the pushing of the actuating button 70 is stopped, the biasing member 76 urges the actuating button 70 back into the first operating configuration. The first operating configuration may then be secured again by the securing member 79.

Referring again to FIG. 1 and to FIGS. 24 to 27, the coupling portions 50 are arranged on one side of a plane spanned by the positioning member 30 and the guide members 36, 36', while the actuating portions 67 of the pivot position fixing members 63 are arranged on an opposite side of the plane spanned by the positioning member 30 and the guide members 36, 36'. Moreover, the coupling portions 50 are oriented such that the lower end 50b faces towards the bone anchors 10, 10'. As shown in FIGS. 26 and 27, the coupling portions 50 are preferably pivotable in a range such that each coupling portion can be pivoted at around 900 from one stop 62a to the other stop 62b. Hence, if the coupling portions 50 are pivoted away from each other as shown in FIG. 26, they can form an open angle α, which may be up to about 270°. When the coupling portions 50 are pivoted towards each other, they can form an angle β of up to about 90° as shown in FIG. 27. Depending on the design of pivot angle limiting structure, other ranges could also be accomplished.

The bone anchors, more specifically, the bone anchoring element 1, the receiver 5, and other parts of the bone anchor as well as the rod 6 and the instrument 100 may each be made of biocompatible materials, for example, of titanium or stainless steel, of a biocompatible alloy, such as NiTi-alloys, for example, Nitinol, of magnesium or magnesium alloys, or from a biocompatible plastic material, such as, for example, polyether ether ketone (PEEK) or poly-l-lactide acid (PLLA). In addition, the parts can be made of the same material or materials, or of different materials from one another.

As illustrated in FIGS. 28a to 30b, one embodiment of use of the instrument 100 together with the bone anchors 10, 10' will be explained. Referring to FIGS. 28a to 28e, first, steps of placing the bone anchors 10, 10' will be explained. The exemplary embodiment is shown with two bone anchors placed into adjacent vertebrae. Depending on the application, a multitude of bone anchors may be placed in a multitude of vertebrae, also on both sides of the sagittal plane. The bone anchors 10, 10' shown in the Figures are of a bottom-loading type, wherein the bone anchoring element 1 can be inserted first into the bone, respectively in the pedicle of a vertebra, as depicted in FIG. 28*a*, and the receiver can be mounted thereafter, as depicted in FIG. 28*b*. In some applications, in particular in MIS, this facilitates easier finding of the correct location where the bone anchor has to be placed and/or offers more space for the placement step.

Once the shanks 2 of the bone anchors 10, 10' have been inserted, the receivers 5 together with the locking rings 13 are mounted onto the heads 3. Next, as shown in FIGS. 28*c* and 28*d*, an instrument 200 that preferably comprises the inner tubular portion 14 and the outer tubular portion 15, as shown in FIGS. 3 and 4, is attached to the receiver 5 and the locking ring 13 of one or both of the bone anchors, respectively, to permit the angular position of the receiver 5 relative to the shank 2 to be locked and/or released. For example, first, the angular position of one bone anchor 10 may be locked. Then, a stabilization rod 6 may be inserted into the receivers 5. Also, the fixation screws 12 (not shown here) may be inserted. Thereafter, the angular position of the second bone anchor 10' may be locked. As the rod 6 and the fixation screws 12 are inserted, but not yet fixed, the rod 6 can still move up and down to a certain extent. After removal of the instrument 200 as shown in FIG. 28*e*, the angular position of the receivers 5 relative to the shanks 2 can remain locked, without interaction with an instrument and without interaction with the rod 6.

Figure 29C:
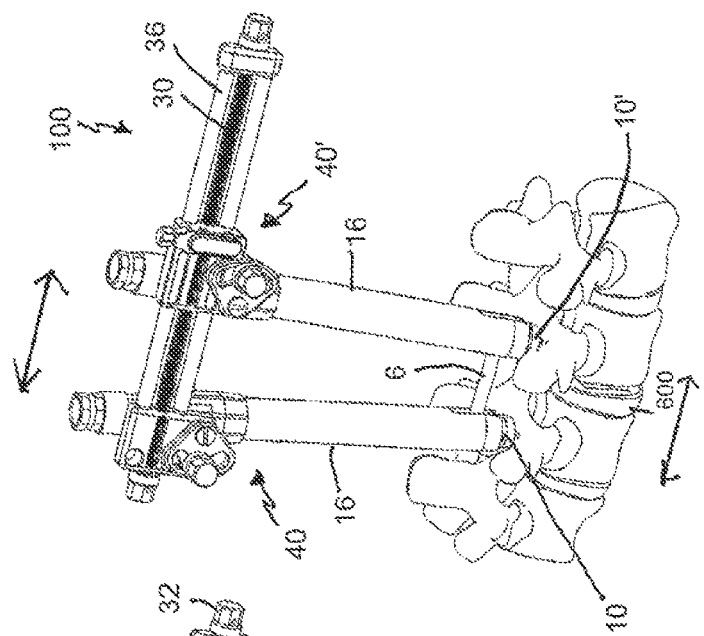
FIGS. 29a to 29c show steps of attaching the instrument to the bone anchors of FIG. 28e and performing distraction on the vertebrae according to an embodiment.
Figure 29B:
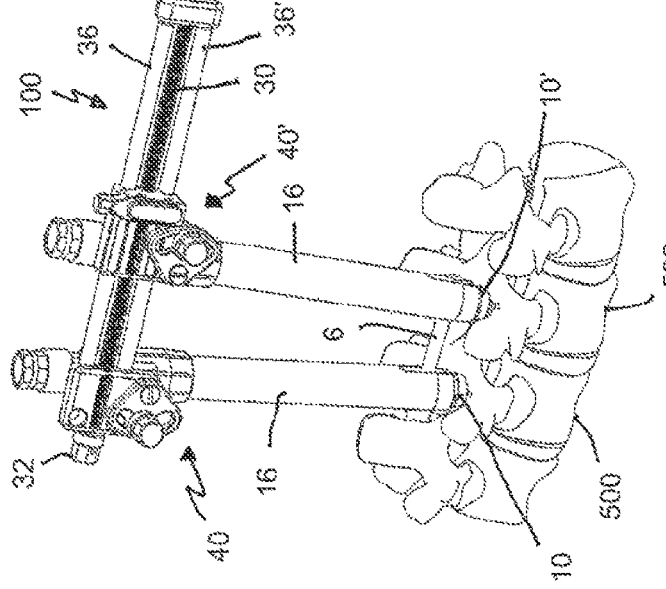
Figure 29A:
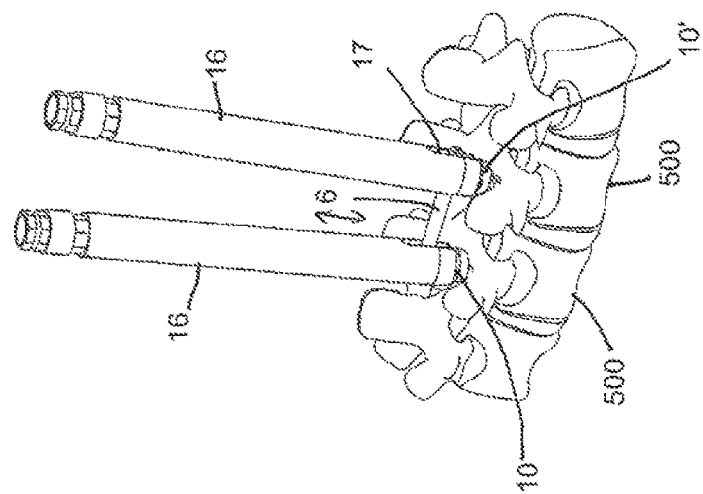

Next, as shown in FIG. 29*a*, screw extenders 16 or repositioning sleeves may be mounted onto the receivers 5. Still, the stabilization rod 6 and the fixation screw 12 may be within the rod receiving recess of the receivers 5, but not yet fixed. The screw extenders 16 may have elongate recesses 17 on the side facing the receiving parts, so that the rod can still move up and down to some extent. Thereafter, the instrument 100 is attached to the screw extenders 16, as shown in FIG. 29*b*. The coupling portions 50, which are pivotable, are placed over the tubular screw extenders 16 and fixed via the fixation members 57 (FIG. 5). To adapt the instrument 100 to the angular position of the receivers that had been locked before, the coupling portions 50 may be pivoted and the specific pivot positions may be fixed by the pivot position fixing members 63. Finally, as shown in FIG. 29*c*, the second coupling member 40' can be translated on the positioning member 30 and the guide members 36, 36', for example, moved away from the first coupling member 40, to perform a distraction of the vertebrae (parallel distraction). The movement can be carried out incrementally when the translation movement actuating mechanism is in the first operating configuration, or can be continuously sliding when the translation movement actuating mechanism is in the second operating configuration. After distraction of the adjacent vertebrae the intervertebral disk 600 may be removed and a cage may be inserted (not shown). Thereafter the instrument 100 may be removed and the rod 6 may be fixed with the fixation members 12.

As shown in FIGS. 29*a* to 29*c*, since the angular positions of the receivers 5 relative to the shanks 2 are locked, the bone anchors 10, 10' act like monoaxial bone anchors which have the shank in a fixed position relative to the receiver. However, compared to known monoaxial bone anchors, the bone anchors permit application of the instrument in an improved manner, since the fixed angles of the receivers relative to the shanks can be selected. Hence, distraction or compression to adjust the sagittal balance to treat kyphosis or lordosis can be more easily facilitated. The two guide rods 36, 36' contribute in taking over loads that act while the distraction takes place.

Another exemplary embodiment of use will be explained with reference to FIGS. 30*a* to 30*b*.

In FIG. 30*a*, the angular positions of the receivers 5 relative to the shanks 2 have also been locked beforehand, and the rod 6 and optionally the fixation screws 12 have been inserted, but are not yet fixed. The instrument 100 is placed onto the receivers 5, while the coupling portions 50 are both pivotable. The second coupling member 40' is in the first condition, meaning that the distance from the first coupling member 40 can be varied incrementally. A correct or desired distance between the coupling members 40, 40' is adjusted. Holders 300 with handles 301 are placed on the screw extenders 16 by engaging them with a front ring portion 302. Then, as depicted in FIG. 30*b*, the holders 300 are moved upward, thereby spreading the screw extenders 16 apart from each other. Also the second coupling member 40' may be moved apart from the first coupling member 40. Thereby, the intervertebral space can be enlarged. As soon as the desired distraction has taken place, the angular position of the coupling portions 50 can be fixed by the pivot position fixing members 63. After optionally having carried out additional steps, the instrument 100 can be removed and the rod 6 can be fixed by the fixation screws 12.

Also in this case, the angular position of the receivers relative to the shanks remain in the previously locked condition without interaction with an instrument and/or without interaction with the rod.

Modifications of the above-described embodiments are also conceivable. It shall be noted that the details of the fixation or connection between two parts are only exemplary, and can be achieved by other means. For the bone anchors, any bone anchor can be used that permits locking of the angular position of the receiver relative to the shank, and where the locked position can be held or maintained irrespective of the presence and/or the position of the rod in the receiver. At least one of two bone anchors has to be a polyaxial bone anchor where the angular position can remain locked without interaction with an instrument and/or without interaction with the rod. The other bone anchor may be a conventional polyaxial or monoaxial bone anchor.

Moreover, the instrument 100 can also be functional with only one guide member, and with the second guide member omitted. However, the two guide members on opposite sides of the positioning member render the instrument particularly stable, in view of the forces that have to be transmitted when performing distraction, repositioning, or compression steps.

It may also be conceivable that both coupling members are movable on the positioning member. In this case, a mounting portion for the first coupling member may be similar to the mounting portion of the second coupling member. It may also be conceivable that only one coupling member is pivotable relative to the positioning member.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A system for correcting a position of bones, bone parts, or vertebrae, the system comprising:
    a first bone anchor comprising a first shank for anchoring in bone and a first receiver for receiving and connecting a rod to the first shank;
    a second bone anchor comprising a second shank for anchoring in bone and a second receiver for receiving and connecting the rod to the second shank; and
    an instrument comprising:
        a positioning member having a longitudinal axis;
        an elongate first guide member that extends substantially parallel to the positioning member;
        a first coupling member for coupling the positioning member to the first bone anchor, wherein the first coupling member is pivotable relative to the positioning member around a first axis that is transverse to the longitudinal axis; and
        a second coupling member for coupling the positioning member to the second bone anchor, wherein the second coupling member is movable translationally along the longitudinal axis of the positioning member with guidance from the first guide member to adjust a distance between the first coupling member and the second coupling member, and is pivotable relative to the positioning member around a second axis, the second axis being both transverse to the longitudinal axis and spaced apart from the positioning member, the first guide member, and the area between the positioning member and the first guide member, while a translational position of the second coupling member relative to the positioning member remains constant;
    wherein at least the first receiver is pivotable relative to the first shank, and wherein the first bone anchor is configured to assume a locked configuration in which an angular position of the first receiver relative to the first shank is locked while the rod remains movable relative to the first receiver.

2. The system of claim 1, wherein the first bone anchor is configured to assume the locked configuration while the rod is not connected to the first receiver.

3. The system of claim 1, wherein the first coupling member and the second coupling member are movable relative to one another on the positioning member.

4. The system of claim 1, wherein at least one of the first coupling member or the second coupling member is connectable to the respective bone anchor via an extension member.

5. The system of claim 4, wherein the extension member comprises a tubular portion.

6. The system of claim 1, wherein the second receiver is pivotable relative to the second shank, and wherein the second bone anchor is configured to assume a locked configuration in which an angular position of the second receiver relative to the second shank is locked while the rod remains movable relative to the second receiver.

7. The system of claim 1, wherein the first coupling member and the second coupling member are connectable to the first bone anchor and the second bone anchor, respectively, while the rod is received by the respective receivers of the first bone anchor and the second bone anchor.

8. The system of claim 1, wherein a pivot position of at least one of the first or second coupling members relative to the positioning member can be fixed.

9. The system of claim 1, wherein at least one of the first or second coupling members comprises a coupling portion and an actuator comprising a projection to facilitate the pivoting of the coupling portion.

10. The system of claim 9, wherein the coupling portion and the actuator are arranged at opposite sides of the positioning member from one another.

11. The system of claim 1, wherein at least one abutting surface is provided for limiting the pivoting of at least one of the first or second coupling members.

12. The system of claim 11, wherein the at least one abutting surface comprises two abutting surfaces for limiting the pivoting of the at least one coupling member to a range of pivot angles.

13. The system of claim 1, wherein a first engagement surface of the positioning member is configured to facilitate an incremental movement of the first coupling member and the second coupling member relative to one another along the longitudinal axis.

14. The system of claim 13, wherein the positioning member comprises a first end and a second end, and wherein the incremental movement of the first coupling member and the second coupling member relative to one another can be effected by actuating the positioning member from the first end or the second end.

15. The system of claim 13, wherein in a first operating configuration the second coupling member engages the first engagement surface of the positioning member to facilitate the incremental movement, and wherein in a second operating configuration the second coupling member is disengaged from the first engagement surface to facilitate a slidable movement between the first coupling member and the second coupling member along the longitudinal axis of the positioning member.

16. The system of claim 15, wherein the second coupling member comprises a second engagement surface configured to engage and disengage the first engagement surface of the positioning member to adjust the second coupling member between the first operating configuration and the second operating configuration.

17. The system of claim 1, wherein the first guide member has a substantially smooth surface.

18. The system of claim 1, wherein the instrument further comprises an elongate second guide member that extends substantially parallel to the first guide member.

19. The system of claim 18, wherein the second guide member is located at a side of the positioning member opposite to a side on which the first guide member is located.

20. The system of claim 1, wherein the first receiver comprises an expandable and compressible head receiving portion for receiving and pivotably holding a head formed at an end portion of the first shank, and a locking ring configured to compress the head receiving portion to lock the head in the head receiving portion.

21. An instrument for correcting a position of bones, bone parts, or vertebrae, the instrument comprising:
    a positioning member having a longitudinal axis;
    a first coupling member with a first single coupling portion connectable to a first bone anchor for coupling the first bone anchor to the positioning member;
    a second coupling member with a second single coupling portion connectable to a second bone anchor for coupling the second bone anchor to the positioning member, wherein the second coupling member and the first coupling member are movable relative to one another along the longitudinal axis; and
    an elongate first guide member and an elongate second guide member that are completely separate parts from one another and arranged at opposite sides of the positioning member from one another, such that the first guide member, the second guide member, and the positioning member extend along a first plane;

wherein at least one of the first coupling member or the second coupling member is configured to simultaneously contact the first guide member, the second guide member, and the positioning member, and wherein at least one of the first single coupling portion or the second single coupling portion is pivotable relative to the positioning member around an axis, wherein the axis is both perpendicular to the first plane and spaced apart from the first guide member, the second guide member, and the area between the first and second guide members.

22. A method for correcting a position of bones, bone parts, or vertebrae using a system comprising a first bone anchor comprising a first shank for anchoring in bone and a first receiver for receiving and connecting a rod to the first shank, a second bone anchor comprising a second shank for anchoring in bone and a second receiver for receiving and connecting the rod to the second shank, and an instrument comprising a positioning member having a longitudinal axis, an elongate first guide member that extends substantially parallel to the positioning member, a first coupling member for coupling the positioning member to the first bone anchor, wherein the first coupling member is pivotable relative to the positioning member around a first axis that is transverse to the longitudinal axis, and a second coupling member for coupling the positioning member to the second bone anchor, wherein the second coupling member is movable translationally along the longitudinal axis of the positioning member with guidance from the first guide member to adjust a distance between the first coupling member and the second coupling member, and is pivotable relative to the positioning member around a second axis, the second axis being both transverse to the longitudinal axis and spaced apart from the positioning member, the first guide member, and the area between the positioning member and the first guide member, while a translational position of the second coupling member relative to the positioning member remains constant, the method comprising:

respectively inserting the first bone anchor and the second bone anchor into a bone or vertebra;

pivoting and adjusting an angular position of at least the first receiver relative to the first shank;

locking the angular position of the first receiver relative to the first shank for the first bone anchor while the rod remains movable relative to the first receiver; and coupling the first coupling member to the first bone anchor and coupling the second coupling member to the second bone anchor.

23. The method of claim 22, further comprising inserting a rod into the respective receivers of the first bone anchor and the second bone anchor prior to coupling the first coupling member to the first bone anchor and coupling the second coupling member to the second bone anchor.

24. The method of claim 22, wherein the instrument further comprises an elongate second guide member that is a completely separate part from the first guide member, that is arranged at an opposite side of the positioning member than the first guide member, and that extends parallel to the positioning member.

25. The system of claim 18, wherein the first and second guide members are completely separate parts from one another.

* * * * *

UNITED STATES PATENT AND TRADEMARK OFFICE
CERTIFICATE OF CORRECTION

| | | |
|---|---|---|
| PATENT NO. | : 11,737,791 B2 | Page 1 of 1 |
| APPLICATION NO. | : 16/594691 | |
| DATED | : August 29, 2023 | |
| INVENTOR(S) | : Timo Biedermann et al. | |

It is certified that error appears in the above-identified patent and that said Letters Patent is hereby corrected as shown below:

In the Specification

Column 12, Line 44        Delete "900" and
Insert -- 90° --

Signed and Sealed this
Thirty-first Day of October, 2023

*Katherine Kelly Vidal*

Katherine Kelly Vidal
*Director of the United States Patent and Trademark Office*